US009968323B2

(12) United States Patent
Yamazaki (10) Patent No.: US 9,968,323 B2
(45) Date of Patent: May 15, 2018

(54) X-RAY COMPUTED TOMOGRAPHY APPARATUS

(71) Applicant: Toshiba Medical Systems Corporation, Otawara-shi (JP)

(72) Inventor: Masahiko Yamazaki, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 252 days.

(21) Appl. No.: 14/700,193

(22) Filed: Apr. 30, 2015

(65) Prior Publication Data
US 2015/0230772 A1 Aug. 20, 2015

Related U.S. Application Data

(63) Continuation of application No. PCT/JP2013/084364, filed on Dec. 20, 2013.

(30) Foreign Application Priority Data

Dec. 21, 2012 (JP) .................................. 2012-279563

(51) Int. Cl.
*A61B 6/00* (2006.01)
*A61B 6/03* (2006.01)
*G06T 11/00* (2006.01)

(52) U.S. Cl.
CPC ............ *A61B 6/5205* (2013.01); *A61B 6/032* (2013.01); *G06T 11/005* (2013.01)

(58) Field of Classification Search
CPC ....... A61B 6/032; A61B 6/5205; A61B 6/548; A61B 6/4028; A61B 6/4291; A61B 6/035; A61B 6/482; A61B 6/50; A61B 2017/00716; A61B 2017/00725; A61B 5/055; A61B 6/027; A61B 6/037; A61B 6/5282; A61B 6/583; A61B 90/36; A61B 6/06; A61B 6/4233; A61B 6/03; A61B 6/4266; A61B 6/4241; A61B 6/4078; A61B 6/4085;
(Continued)

(56) References Cited

U.S. PATENT DOCUMENTS 4,747,117 A * 5/1988 Albrecht ................ A61B 6/032
250/366
5,268,757 A 12/1993 Nagai et al.
(Continued)

FOREIGN PATENT DOCUMENTS

JP 56-33908 4/1981
JP 4-53539 A 2/1992
(Continued)

OTHER PUBLICATIONS

International Search Report dated Jan. 28, 2014 for PCT/JP2013/084364 Filed on Dec. 20, 2013 (English Language).
(Continued)

*Primary Examiner* — Irakli Kiknadze
(74) *Attorney, Agent, or Firm* — Oblon, McClelland, Maier & Neustadt, L.L.P.

(57) ABSTRACT

An X-ray computed tomography apparatus according to an embodiment includes an X-ray detector, a data-acquisition module and a reconstruction module. In the X-ray detector, a plurality of X-ray detection elements are arranged in a channel direction and a column direction. The data-acquisition module includes a plurality of data-acquisition circuits and a plurality of output modules. A plurality of systems of at least the data-acquisition circuits among the X-ray detection elements and the data-acquisition circuits are disposed in parallel per element of the X-ray detection elements in a center vicinity. Each of the output modules outputs digital data obtained via the data-acquisition circuits. The reconstruction module reconstructs a medical image, based on the output digital data.

15 Claims, 9 Drawing Sheets

(58) Field of Classification Search
CPC ......... A61B 6/5235; A61B 6/54; A61B 6/025;
A61B 6/0457; A61B 6/4441; A61K
31/506; A61K 47/48969; A61K 9/08;
B82Y 5/00; C08B 37/0012; C08B
37/0015; C08L 5/16; G06T 11/005; G06T
2200/04; G06T 11/003; G06T 11/00;
H01L 27/14658; H04N 5/32; H04N
5/335; H04N 5/378
USPC .............................................. 378/4, 19, 89.8
See application file for complete search history.

(56) References Cited

U.S. PATENT DOCUMENTS

| | | | | |
|---|---|---|---|---|
| 6,215,843 | B1 * | 4/2001 | Saito | G01N 23/046 250/370.09 |
| 6,535,571 | B2 * | 3/2003 | Von Der Haar | A61B 6/032 250/370.09 |
| 7,522,695 | B2 * | 4/2009 | Nishide | A61B 6/032 250/370.09 |
| 2002/0191737 | A1 | 12/2002 | Tanigawa | |
| 2010/0260313 | A1 | 10/2010 | Kudo et al. | |

FOREIGN PATENT DOCUMENTS

| | | |
|---|---|---|
| JP | 2001-212128 A | 8/2001 |
| JP | 2002-345803 A | 12/2002 |
| JP | 2010-259781 A | 11/2010 |

OTHER PUBLICATIONS

International Written Opinion dated Jan. 28, 2014 for PCT/JP2013/084364 Filed on Dec. 20, 2013.

* cited by examiner

this application claims …

X-RAY COMPUTED TOMOGRAPHY APPARATUS

CROSS-REFERENCE TO RELATED APPLICATIONS

This application is a Continuation application of PCT application No. PCT/JP2013/084364, filed on Dec. 20, 2013, and is based upon and claims the benefit of priority from Japanese Patent Application No. 2012-279563, filed on Dec. 21, 2012; the entire contents of which are incorporated herein by reference.

FIELD

Embodiments described herein relate generally to an X-ray computed tomography apparatus.

BACKGROUND

Conventional X-ray computed tomography apparatuses (hereinafter referred to as X-ray CT apparatuses) are mainly comprised of third-generation X-ray CT apparatuses.

In the third-generation X-ray CT apparatus, an X-ray tube and an X-ray detector as a pair are rotated around a subject, and X-rays, which have passed through the subject, are detected by a plurality of X-ray detection elements included in the X-ray detector. Incidentally, the respective X-ray detection elements are arrayed in a grid shape in a channel direction which is perpendicular to the body axis of the subject, and in a column direction along the body axis of the subject.

Detection signals of detected analog quantities are sequentially read out to a data-acquisition module (data acquisition system (DAS)) from read-out lines associated with respective channels via switches which are changed over on a column-by-column basis. This read-out method is called a "sequential acquisition method".

The data-acquisition module includes an amplifier and an A/D conversion module, which are provided in association with each of the plural X-ray detection elements, and a control board. The amplifier and A/D conversion module amplify the detection signal acquired from each X-ray detection element, and then convert the detection signal to digital data. The control board sends this digital data to a reconstruction module.

The reconstruction module reconstructs an image relating to the subject, based on the sent detection data.

However, in the X-ray CT apparatus as described above, data-acquisition modules, which are connected to the elements arranged near the center in the channel direction (hereinafter, also referred to as "channel center"), always acquire the same projection data from X-rays which have passed through the rotational center. Thus, if there is a variance in characteristics between the elements or the data-acquisition modules, a ring artifact of a diameter corresponding to the variance tends to occur. In particular, the variance in characteristics between the elements or the data-acquisition modules in the vicinity of the channel center tends to generate an artifact in inverse proportion to a square root of the radius from the channel center. It is thus required that the variance in characteristics between the elements and between the data-acquisition modules in the vicinity of the channel center be as small as possible.

For example, in the case of such characteristics that the linearity of the amplifier and A/D conversion module (QV/ADC) connected to the element varies from chip to chip, there is a case in which an artifact occurs due to the difference in responsivity between chips. On the other hand, it is very difficult to uniformize the characteristics of individual chips, from the standpoint of the present measurement techniques, yields, etc.

The object is to provide an X-ray computed tomography apparatus which can prevent the occurrence of an artifact corresponding to the variation in characteristics in the elements or data-acquisition systems in the vicinity of the channel center.

DETAILED DESCRIPTION

In general, according to one embodiment, an X-ray computed tomography apparatus includes an X-ray generator, an X-ray detector, a data-acquisition module, and a reconstruction module.

The X-ray generator is configured to generate X-rays.

The X-ray detector is configured such that a plurality of X-ray detection elements are arranged in a grid shape in a channel direction perpendicular to a body axis of the subject and in a column direction along the body axis of the subject.

The plurality of X-ray detection elements detect the X-rays that have been generated from the X-ray generator and have passed through a subject, and detection signals are read out from the X-ray detection elements.

The data-acquisition module includes a plurality of data-acquisition circuits and a plurality of output modules.

The plurality of data-acquisition circuits are configured to acquire the detection signals individually read out from the X-ray detection elements, to amplify the acquired detection signals individually, and to convert the detection signals to digital data.

The plurality of output modules are configured to output the converted digital data individually.

The reconstruction module is configured to reconstruct a medical image, based on the output digital data.

A plurality of systems of at least the data-acquisition circuits among the X-ray detection elements and the data-acquisition circuits are disposed in parallel per element of the X-ray detection elements in a center vicinity.

Each of the output modules, which are connected to the data-acquisition circuits disposed in parallel, is configured to output digital data obtained via the data-acquisition circuits.

An X-ray CT apparatus according to an embodiment will now be described with reference to the accompanying drawings.

Figure 1:
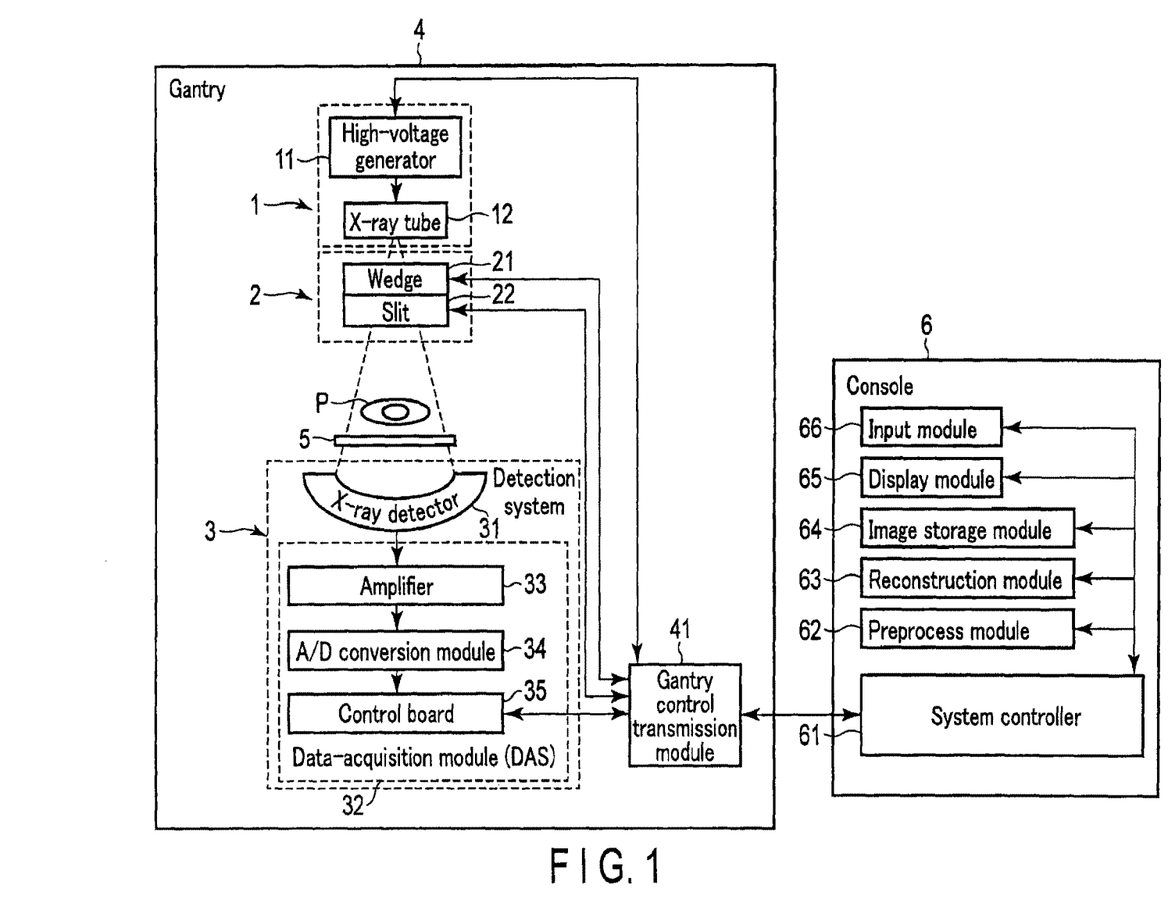
FIG. 1 is a block diagram illustrating a configuration of an X-ray CT apparatus according to an embodiment.

FIG. 1 is a block diagram illustrating a configuration of an X-ray CT apparatus according to an embodiment. In this X-ray CT apparatus, as illustrated in FIG. 1, a gantry 4 and a console 6 are electrically connected. In the gantry 4, a pair of systems consisting of an X-ray system 1 and an optical system 2, on the one hand, and a detection system 3, on the other hand, are accommodated, and a rotational support mechanism (not shown), which rotates the pair of systems about a body axis of a subject P on a table 5, is accommodated. The rotational support mechanism includes a rotary ring, a ring support mechanism which supports the rotary ring so as to be rotatable about a rotational axis Z, and a driving module for driving the rotation of the ring. An X-ray tube 12 and an X-ray detector 31 of a so-called two-dimensional array type or a multi-column type are mounted on the rotary ring. At a time of imaging or scanning, the subject P is placed on the table 5 in a cylindrical imaging region between the X-ray tube 12 and the X-ray detector 31 in the gantry 4.

The X-ray system 1, optical system 2 and detection system 3 are controlled by a gantry control transmission module 41 in the gantry 4. The gantry control transmission module 41 is transmissibly connected to a system controller 61 in the console 6. The console 6 includes the system controller 61, a preprocess module 62, a reconstruction module 63, an image storage module 64, a display module 65 and an input module 66.

The X-ray system 1 includes a high-voltage generator 11 and X-ray tube 12.

The high-voltage generator 11 includes a high-voltage power supply (not shown) for applying a high voltage between an anode target and a cathode filament of the X-ray tube 12, and a filament current generator (not shown) for supplying a filament current to the cathode filament of the X-ray tube 12.

The X-ray tube 12 generates X-rays by receiving the application of the voltage (hereinafter referred to as a tube voltage) and the supply of the filament current from the high-voltage generator 11 via a slip ring (not shown), and radiates the X-rays from the focal point of X-rays. The X-rays radiated from the focal point of X-rays are shaped, for example, in a cone beam shape (pyramidal shape), via a wedge 21 and a slit 22 in the optical system 2 attached to an X-ray radiation window of the X-ray tube 12. Incidentally, the wedge 21 is a filter for reducing radiation exposure, and the slit 22 is a gap for beam shaping. The radiation range of X-rays is indicated by a broken line. An X axis is a straight line which is perpendicular to the rotational axis Z and passes through the focal point of radiated X-rays. A Y axis is a straight line which is perpendicular to the X axis and the rotational axis Z. It is assumed that the X-ray tube 12 in the present embodiment is an X-ray tube of a rotary anode type. Incidentally, X-ray tubes of other types, excluding an X-ray tube of a fixed anode type, are also applicable to the present embodiment.

On the other hand, the detection system 3 includes the X-ray detector 31 and a data-acquisition module (DAS) 32.

The X-ray detector 31 is attached at such a position and an angle as to be opposed to the X-ray tube 12, with the rotational axis Z interposed. The X-ray detector 31 includes a plurality of X-ray detection elements which are arrayed in a grid shape in a channel direction which is perpendicular to the body axis of the subject P (or the direction of the rotational axis Z), and in a column direction along the body axis of the subject P. A collimator, which narrows the directivity of incoming X-rays, is attached to each of the plural X-ray detection elements. Each of the plural X-ray detection elements detects X-rays which have been generated from the X-ray tube 12 and have passed through the subject P. For example, X-rays, which have passed through the subject P, are incident on the X-ray detection element. The X-rays incident on the X-ray detection element are narrowed by the collimator, made incident on a scintillator, and converted to visible light. The visible light enters a photodiode and generates an electric charge, and the stored charge is released by a bias voltage applied to the photodiode. The released charge is stored through a read-out line by a CMOS switch functioning as a read-out switch, and is read out as a detection signal. Detection signals from the plural X-ray detection elements are output to the data-acquisition module (DAS) 32 via a connection switch module (not shown). The channel direction may be a direction of an arc which is perpendicular to the rotational axis Z, has a center at a focal point of radiated X-rays, and has a radius corresponding to a distance from this center to a middle point of light-reception parts of X-ray detection elements corresponding to one channel. In addition, the column direction may also be called a slice direction. Further, the above configuration for read-out of detector signals is merely an example, and a charge signal from the photodiode may be directly output as a direct current signal to a rear-stage data-acquisition module (DAS), and a semiconductor detector of a direct conversion type, which does not use a scintillator, may be used as the detector.

The data-acquisition module (DAS) 32 includes a plurality of data-acquisition circuits and a plurality of output modules. The plural data-acquisition circuits acquire detection signals which are individually read out from the respective X-ray detection elements, amplify the acquired detection signals individually, and convert the detection signals to digital data. The plural output modules are disposed on a control board 35, and output the converted digital data individually. The number of data-acquisition circuits is less than the number of X-ray detection elements. The data-acquisition circuits, the number of which is equal to the number of output terminals (or switches) of connection switch modules (not shown), are provided, and each data-acquisition circuit is mounted in association with each channel (ch) of each segment. Each data-acquisition circuit may include, for example, an amplifier 33 and an A/D converter. The amplifier 33 amplifies the detection signals received from the X-ray detection elements. The A/D converter 34 converts an output signal of the amplifier 33 to digital data, and outputs the digital data to the gantry control transmission module 41 via the control board 35. This digital data is representative of an X-ray quantity which is incident on the X-ray detector 31. The gantry control transmission module 41 sends this digital data to the preprocess module 62 via the system controller 61.

The preprocess module 62 generates projection data, based on the digital data received from the data-acquisition module 32 via the gantry control transmission module 41 and system controller 61. Specifically, the preprocess module 62 executes a preprocess on the digital data, thereby generating projection data. The preprocess is, for instance, a reference process which detects, by a reference detector, a variation in tube voltage or tube current of the X-ray tube 12, normalizes the digital data in accordance with the detected value, and corrects a variance in X-ray intensity. The projection data is data (raw data) immediately before a reconstruction process, and is a set of data values corresponding to the intensity of X-rays which have passed through the subject. The projection data is associated with data which represents a view angle when data is acquired, and is stored in a storage module (not shown) which includes a magnetic disk, a magnetic optical disk, or a semiconductor memory. For the purpose of convenience in this description, a set of projection data over all channels at the same view angle, which have been acquired at substantially the same time by one shot, is referred to as a projection data set. Incidentally, projection data for each channel of the projection data set is identified by a view angle, a cone angle and a channel number. The view angle represents each position on a circular orbit along which the X-ray tube 12 rotates about the rotational axis Z, by an angle in the range of 360°, with an uppermost part of the circular orbit in a vertically upward direction from the rotational axis X, which is taken as 0°.

The reconstruction module 63 reconstructs a substantially cylindrical three-dimensional image (medical image), based on a projection data set in the range in which the view angle is 360° or 180°+a fan angle.

The image storage module 64 stores volume data which has been generated by the reconstruction module 63. The image storage module 64 stores a tomographic image of the subject, which has been generated by an image processor (not shown).

The display module 65 displays, for example, an image reconstructed by the reconstruction module 63, an image stored in the image storage module 64, and conditions which are set for X-ray computed tomography.

The input module 66 inputs, for example, imaging conditions for X-ray computed tomography desired by an operator, and information about the subject. Specifically, the input module 66 takes various instructions, commands, information, selection and settings from the operator into the X-ray CT apparatus. Although not illustrated, the input module 66 includes a track ball, a switch button, a mouse, a keyboard, etc., for setting a region-of-interest, etc. The input module 66 detects coordinates of a cursor which is displayed on the display screen, and outputs the detected coordinates to the system controller 61. Incidentally, the input module 66 may be a touch panel which is so provided as to cover the display screen. In this case, the input module 66 detects touch-instructed coordinates by a coordinate read principle of an electromagnetic induction method, an electromagnetic strain method, a pressure-sensing method, etc., and outputs the detected coordinates to the system controller 61.

The system controller 61 functions as a central unit of the X-ray CT apparatus. The system controller 61 includes a CPU and a memory (not shown). The system controller 61 controls the table 5, gantry 4 and high-voltage generator 11 for X-ray computed tomography, based on inspection schedule data and a control program stored in a storage module (not shown). Specifically, the system controller 61 temporarily stores in a memory (not shown) information such as operator's instructions and conditions of image processing, which are sent from the input module 66. Based on the information temporarily stored in the memory, the system controller 61 controls the table 5 and gantry 4, and the high-voltage generator 11. The system controller 61 reads out from the memory module (not shown) a control program for executing predetermined image generation/display, develops the control program on its own memory, and executes arithmetic operations/processes, etc., relating to various processes.

Next, a concrete description will be given of the configuration of the detection system 3 in the X-ray CT apparatus having the above-described structure.

Figure 2:
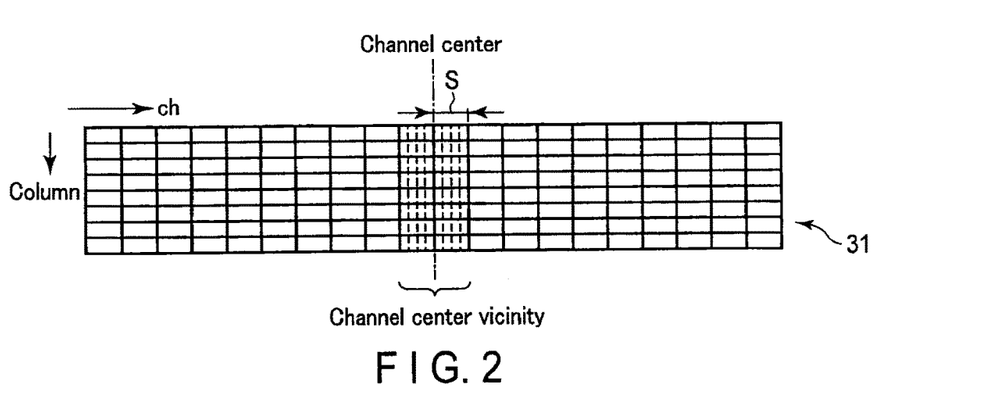
FIG. 2 is a top view of an X-ray detector in the embodiment.
Figure 3:
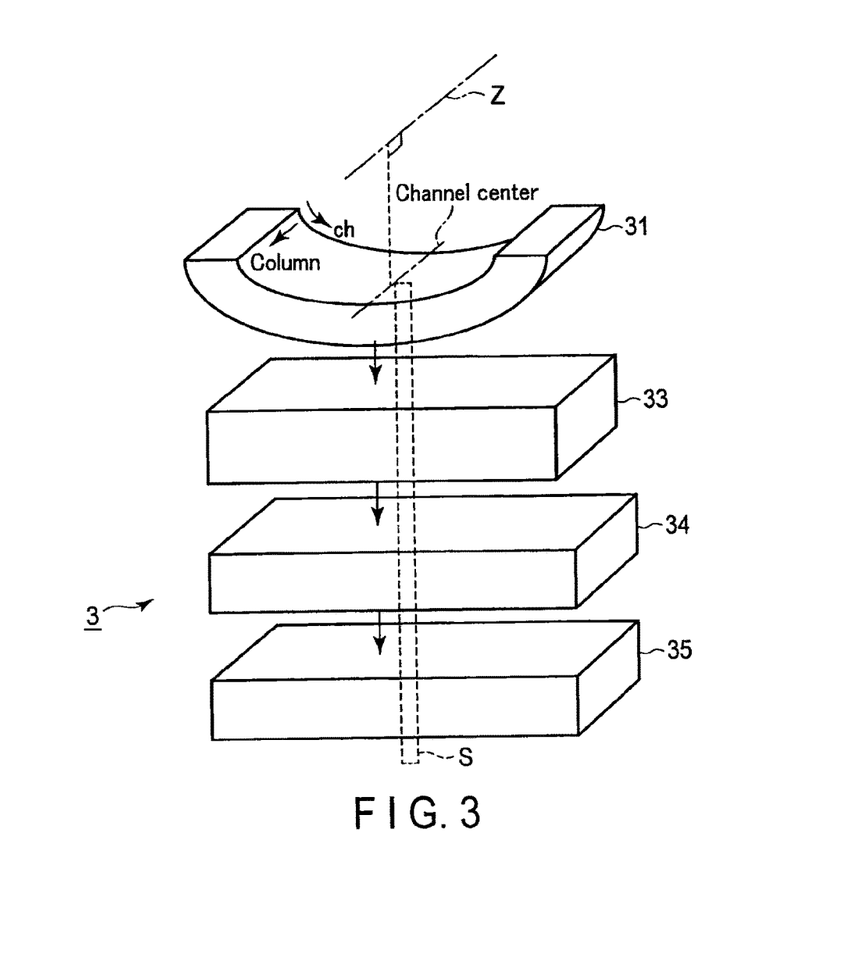
FIG. 3 is a schematic view for explaining a channel center and a subsystem S of a detection system in the embodiment.
Figure 4:
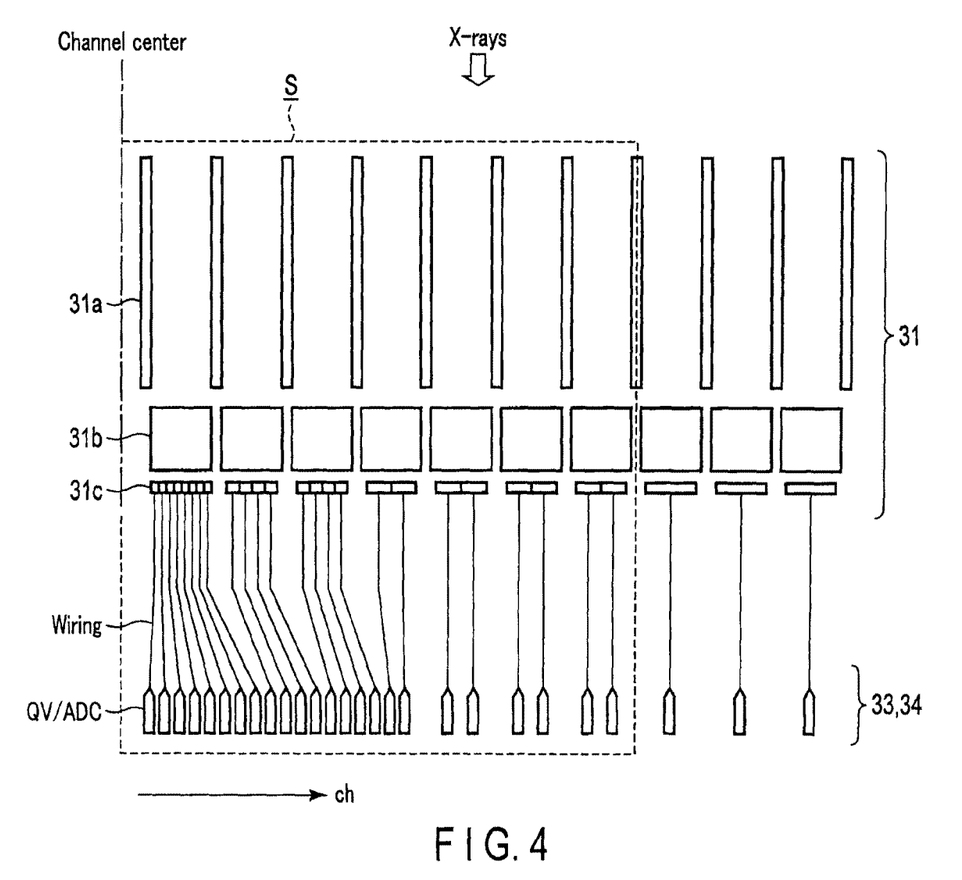
FIG. 4 is a schematic view for describing a configuration of the subsystem S of the detection system in the embodiment.

FIG. 2 is a top view of the X-ray detector 31, and schematically illustrates a center (channel center) in the channel direction, a channel center vicinity, and a subsystem S of the right half of the channel center. FIG. 3 is a schematic view for explaining the channel center and the subsystem S in the detection system 3. FIG. 4 is a schematic view for describing a configuration of the subsystem S in the detection system 3.

In the detection system 3, a plurality of systems of at least data-acquisition circuits among the X-ray detection elements (photodiodes 31c of X-ray detection elements) and data-acquisition circuits (amplifiers 33 and A/D converters 34 of data-acquisition circuits) are disposed in parallel on a channel-by-channel basis in the channel center vicinity. Incidentally, "channel center vicinity" means the vicinity of the center in the channel direction. In addition, a collimator 31a and a scintillator 31b in the X-ray detector 31 are disposed on a channel-by-channel basis. Although the case in which the configuration is applied to the channel direction alone is described by way of example, the configuration is not limited to this example and the configuration may be applied to both the channel direction and the column direction. This applies to all structure examples and modifications to be described below.

In the configuration shown in FIG. 4, both a plurality of systems of X-ray detection elements (photodiodes 31c of X-ray detection elements) and a plurality of systems of data-acquisition circuits (amplifiers 33 and A/D converters 34 of data-acquisition circuits) are disposed in parallel on a channel-by-channel basis in the channel center vicinity. For example, in a first channel from the channel center, eight systems of photodiodes 31c, amplifiers 33 and A/D converters 34 are disposed in parallel. In addition, in second and third channels from the channel center, four systems of photodiodes 31c, amplifiers 33 and A/D converters 34 are disposed in parallel on a channel-by-channel basis. Further, in fourth to seventh channels from the channel center, two systems of photodiodes 31c, amplifiers 33 and A/D converters 34 are disposed in parallel on a channel-by-channel basis.

In more detail, the X-ray detection elements (photodiodes 31c of the X-ray detection elements) are disposed at a higher density in the channel center vicinity than in parts different from the channel center vicinity, and the pitch in the channel direction gradually decreases toward the channel center. The pitch in the channel direction is substantially proportional to the square root of the distance from the channel center. In addition, parts, which are subsequent to the photodiodes 31c in the channel center vicinity, are configured to be disposed with a pitch in the channel direction; the pitch being substantially proportional to the square root of the distance from the channel center.

Figure 5:
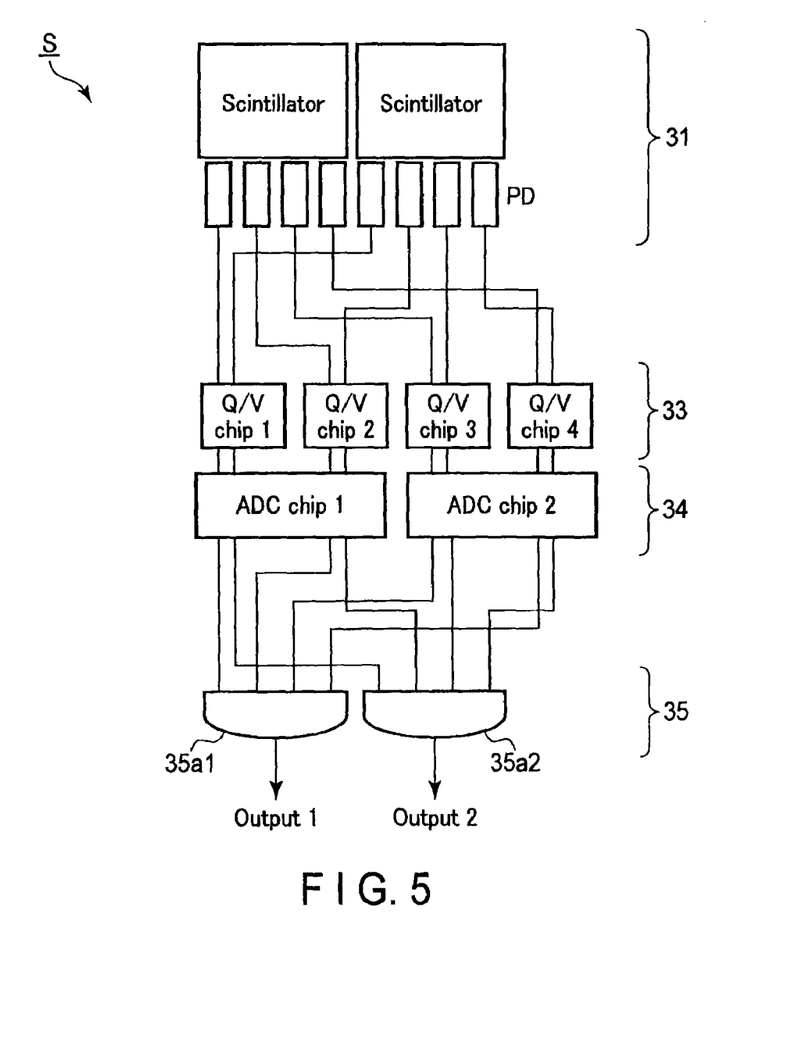
FIG. 5 is a schematic view illustrating an example of a distributed arrangement of chips in the embodiment.
Figure 6:
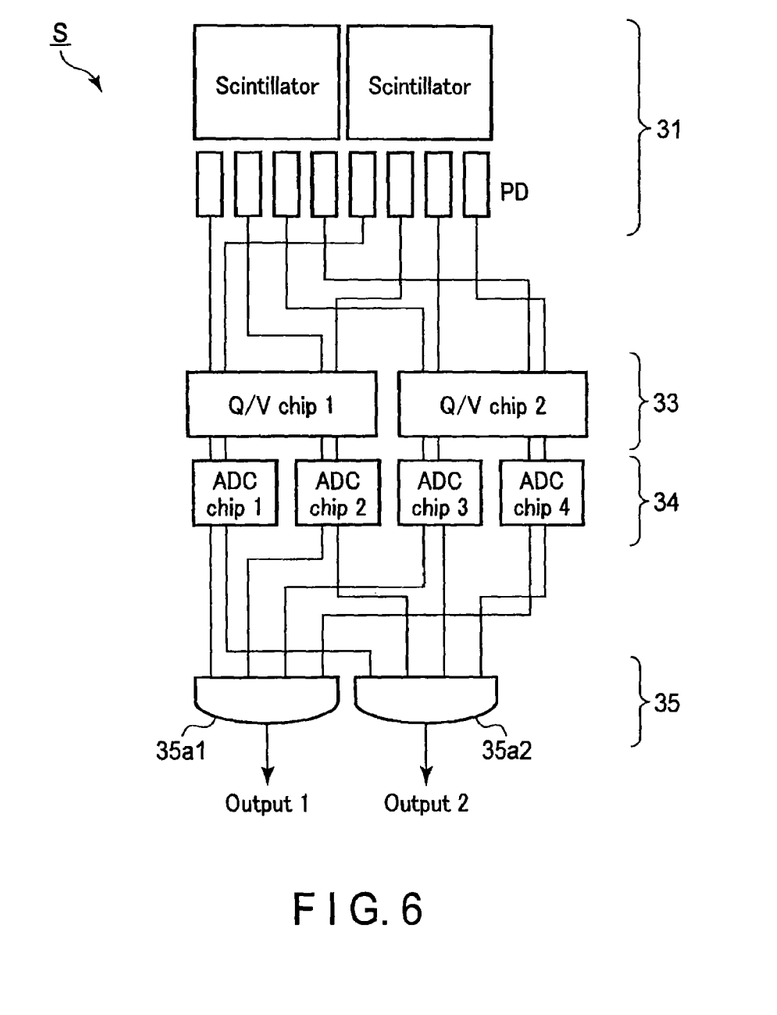
FIG. 6 is a schematic view illustrating another example of the distributed arrangement of chips in the embodiment.

In this case, as illustrated in FIG. 5 or FIG. 6, the amplifiers 33 and A/D converters 34 in the system S in the channel center vicinity may be disposed to be distributed to a plurality of chips. A systematic error in linearity of data-acquisition modules 32 is mainly due to a difference in characteristics between respective chips which constitute data-acquisition modules 32. Thus, if detection signals from the X-ray detector 31, which are to be averaged, are distributed to the respective chips, the variance in chip characteristics can further be averaged.

The averaging can be executed by the control board 35, preprocess module 62, or reconstruction module 63. However, the structure for the averaging is not indispensable, and may be omitted.

Next, a description is given of, for example, the case in which the respective output modules in the control board 35 execute averaging. In FIG. 5 or FIG. 6, of the respective output modules, output modules 35a1, 35a2, . . . , which are connected to the plural systems of data-acquisition circuits which are disposed in parallel on a channel-by-channel basis in the system S, average digital data obtained via the respective data-acquisition circuits and output averaged data. In this case, each output module 35a1, 35a2, . . . , may include a plurality of input terminals which are electrically connected to output terminals of the respective data-acquisition circuits, and one output terminal which is electrically connected to these input terminals. Specifically, each output module 35a1, 35a2, . . . , may combine outputs of the plural systems of data-acquisition circuits disposed in parallel on a channel-by-channel basis, and may connect the outputs to the gantry control transmission module 41. The same applies to the configuration shown in FIG. 4.

In addition, for example, the preprocess module 62 may average the digital data which have been output via the respective output modules from the plural systems of data-acquisition circuits disposed in parallel on a channel-by-channel basis. In this case, the preprocess module 62 executes the preprocess, based on the digital data obtained by the averaging, and the digital data which have been output via the output modules from the data-acquisition circuits disposed in the parts different from the channel center vicinity.

Alternatively, the reconstruction module 63, and not the preprocess module 62, may average the digital data which have been output via the respective output modules from the plural systems of data-acquisition circuits disposed in parallel on a channel-by-channel basis. In this case, the reconstruction module 63 reconstructs a medical image based on the digital data obtained by the averaging and the digital data which have been output via the output modules from the data-acquisition circuits disposed in the parts different from the channel center vicinity.

Figure 7:
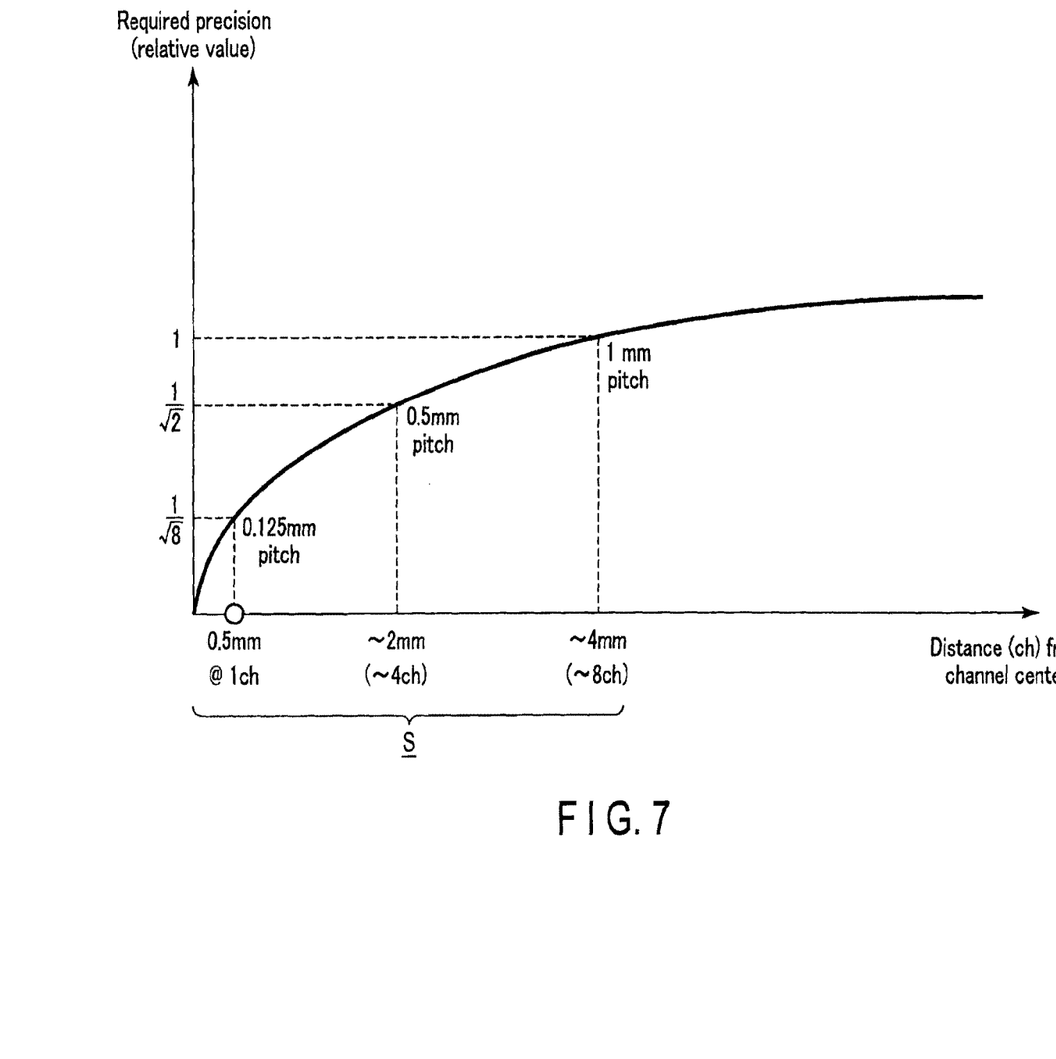
FIG. 7 is a schematic view illustrating a distance from a channel center in the embodiment and a relative precision required for each element.

FIG. 7 is a schematic view illustrating a distance (or the number of channels) from the channel center and a relative precision required for each element. As illustrated, the precision (relative value) required for each element in the system S in the channel center vicinity is reduced in proportion to the square root of the distance (or the number of channels) from the channel center. This corresponds to the fact that the variance in characteristics between the elements or the data-acquisition modules in the channel center vicinity tends to generate artifacts in inverse proportion to the square root of the distance from the channel center.

This being the case, a systematic variance such as linearity of each element is mainly reduced by combining plural elements. For example, a normal 1 mm pitch is set up to about 4 mm (8 CH) from the channel center, and the pitch of elements is halved up to about 2 mm (4 CH) that is half the distance. Then, the pitch of elements is set at ¼ up to about 1 mm (2 CH) that is ¼ of the distance, and the pitch of elements is set at ⅛ up to about 0.5 mm (1 CH) that is ⅛. Thereby, the variance is averaged, and thus the variation precision is reduced to $1/\sqrt{2}$, $1/\sqrt{4}$, $1/\sqrt{8}$, respectively, and the required precision in the graph of FIG. 7 is satisfied.

For example, in association with the required precision "$1/\sqrt{8}$" in FIG. 7, in the present embodiment, the characteristics of at least the eight data-acquisition modules among the eight X-ray detection elements and eight data-acquisition modules in the channel center vicinity are averaged, and the variance is suppressed to "$1/\sqrt{8}$".

Similarly, in association with the required precision "$1/\sqrt{2}$" in FIG. 7, in the present embodiment, the characteristics of at least the two data-acquisition modules among the two X-ray detection elements and two data-acquisition modules in the channel center vicinity are averaged, and the variance is suppressed to "$1/\sqrt{2}$".

In the X-ray CT apparatus according to the embodiment, by averaging the characteristics of the detection system 3 in the channel center vicinity, as described above, it is possible to prevent the occurrence of artifacts corresponding to the variation in characteristics in the elements or data-acquisition systems in the channel center vicinity.

As has been described above, according to the embodiment, at least a plurality of systems of data-acquisition circuits, among the X-ray detection elements and data-acquisition circuits, are disposed in parallel on a channel-by-channel basis in the channel center vicinity. In addition, the output modules 35a1, 35a2, . . . , which are connected to the data-acquisition circuits disposed in parallel, average the outputs of these data-acquisition circuits. Thereby, it is possible to prevent the occurrence of artifacts corresponding to the variation in characteristics in the elements or data-acquisition systems in the channel center vicinity.

In addition, in the case where each output module 35a1, 35a2, . . . , includes a plurality of input terminals and one output terminal which is electrically connected to these input terminals, the outputs of the plural systems of data-acquisition circuits disposed in parallel on a channel-by-channel basis are combined and connected to the gantry control transmission module 41. In this case, the outputs of the data-acquisition circuits can easily be averaged.

Aside from the case in which the output modules 35a1, 35a2, . . . , average the digital data, for example, the preprocess module 62 or reconstruction module 63 may average the output data which have been output via the output modules from the plural systems of data-acquisition circuits disposed in parallel on a channel-by-channel basis. In this case, too, the same advantageous effects as in the present embodiment can be obtained.

Furthermore, even in the case where the X-ray detection elements are disposed at a higher density in the channel center vicinity than in parts different from the channel center vicinity and the pitch in the channel direction gradually decreases toward the channel center, the same advantageous effects as in the present embodiment can be obtained. In this case, such a configuration may be adopted that the pitch in the channel direction is substantially proportional to the square root of the distance from the channel center. Thereby, compared to the case of using a single element, since the variance in characteristics can be reduced to a fraction of the square root of the number of elements to be averaged, the occurrence of artifacts can be prevented. In addition, it is desirable that the data-acquisition circuits, which convert detection signals from the X-ray detection elements disposed at the higher density, be disposed to be distributed to plural chips, from the standpoint of averaging the variance in characteristics in the data-acquisition systems.

Figure 8:
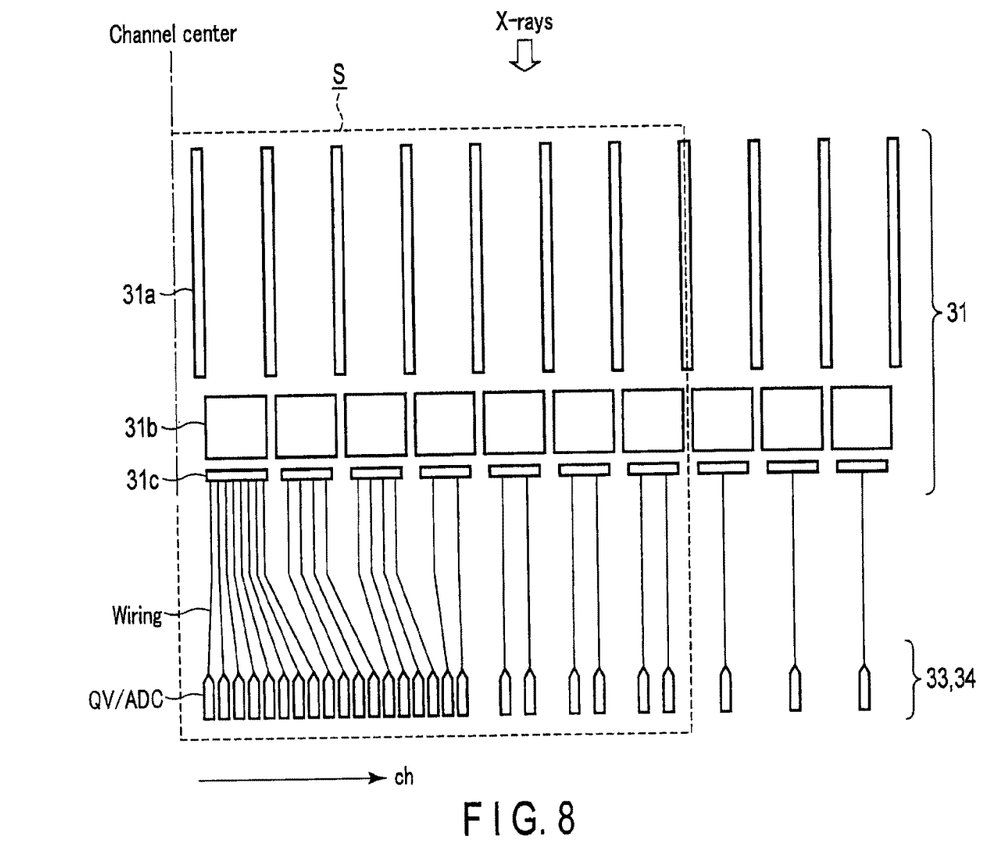
FIG. 8 is a schematic view for describing a modification of the configuration of the subsystem S of the detection system in the embodiment.
Figure 9:
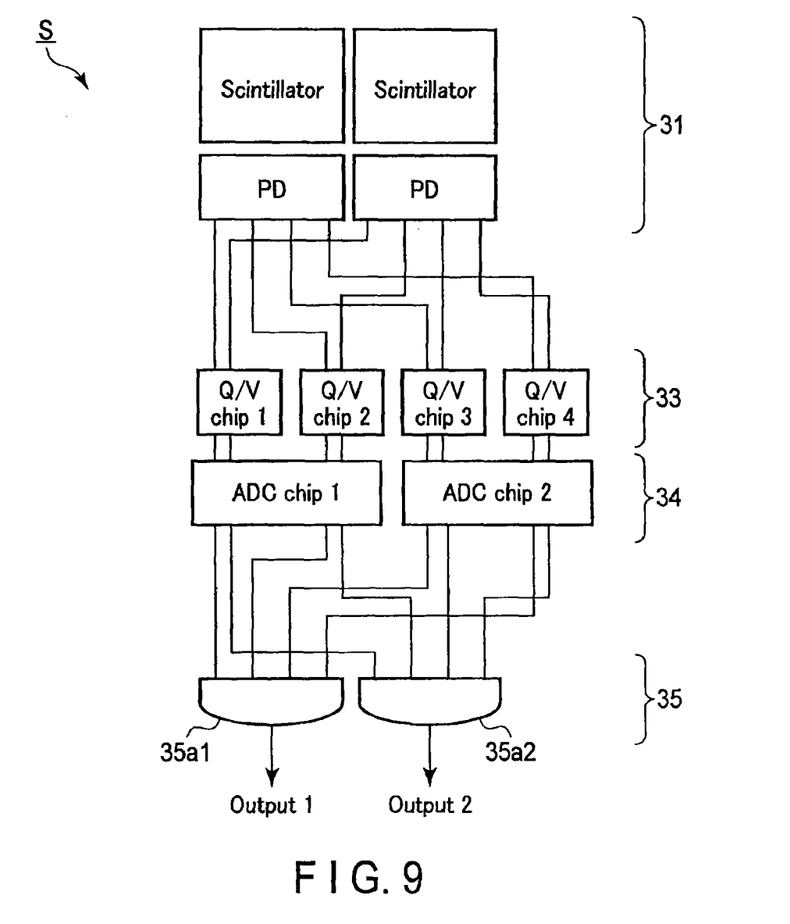
FIG. 9 is a schematic view illustrating another modification of the distributed arrangement of chips in the embodiment.
Figure 10:
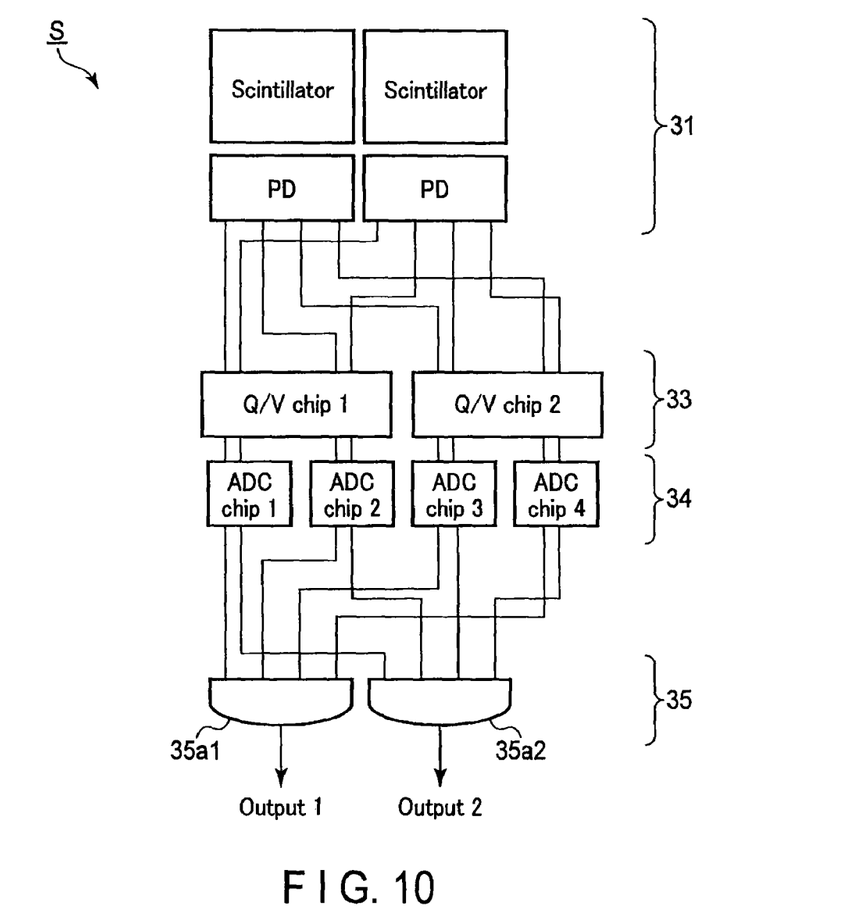
FIG. 10 is a schematic view illustrating still another modification of the distributed arrangement of chips in the embodiment.

In the meantime, the configurations shown in FIG. 4 to FIG. 6 according to the embodiment may be modified as illustrated in FIG. 8 to FIG. 10, respectively. Specifically, such a modification may be made that a plurality of systems of X-ray detection elements (photodiodes 31c of X-ray detection elements) are not disposed on a channel-by-channel basis, and a plurality of systems of only data-acquisition circuits (amplifiers 33 and A/D converts 34 of data-acquisition circuits) are disposed in parallel on a channel-by-channel basis.

In addition, in the embodiment, from the standpoint of suppressing an increase in cost of the data-acquisition module 32 due to an increase in the number of X-ray detection elements in the channel center vicinity, it is possible to suppress an increase in the number of X-ray detection elements of the whole X-ray detector 31 by setting the channel pitch of the peripheral part at a necessary roughness.

Furthermore, in the embodiment, a similar method can be applied to the column direction, as well as the channel direction. In this case, in the detection system 3, a plurality of systems of at least the data-acquisition circuits, among the X-ray detection elements (photodiodes 31c of X-ray detection elements) and the data-acquisition circuits (amplifiers 33 and A/D converts 34 of data-acquisition circuits), are disposed in parallel per element of the X-ray detection elements in the center vicinity. Incidentally, the term "center vicinity" means the vicinity of the center of (a detection surface of) the X-ray detector 31, and means, more specifically, the vicinity of the center in the channel direction and column direction. In addition, the term "per element" corresponds to, for example, "per scintillator 31b" in FIG. 5.

In more detail, the X-ray detection elements (photodiodes 31c of the X-ray detection elements) are disposed at a higher density in the center vicinity than in parts different from the center vicinity, and the pitch in the channel direction and column direction gradually decreases toward the center. The pitch in the channel direction and column direction is substantially proportional to the square root of the distance from the center. In addition, parts, which are subsequent to the photodiodes 31c in the center vicinity, are configured to be disposed with a pitch in the channel direction and column direction, the pitch being substantially proportional to the square root of the distance from the center.

In this case, as illustrated in FIG. 5, FIG. 6, FIG. 9 or FIG. 10, the amplifiers 33 and A/D converters 34 in the system S in the center vicinity may be disposed to be distributed to a plurality of chips. In the meantime, FIG. 9 or FIG. 10 illustrates a configuration example in which, of the X-ray detection elements and data-acquisition circuits, a plurality of systems of only the data-acquisition circuits are disposed in parallel per element of X-ray detection elements in the center vicinity, and the data-acquisition circuits disposed in parallel are disposed to be distributed to plural chips.

As has been described above, in the case of the structure in which the method of the embodiment is applied to both directions (channel direction and column direction), the same advantageous effects as in the present embodiment can be obtained as regards the channel direction. On the other hand, as regards the column direction, unlike the channel direction, there occurs no advantageous effect of preventing or suppressing the occurrence of artifacts at a time of reconstructing an image. However, when an MPR (Multi-Planar Reconstruction) image is composed, such an effect can be obtained that the "connection" between slice images adjacent in the column direction becomes smoother.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus comprising:
an X-ray generator configured to generate X-rays;
an X-ray detector configured such that a plurality of X-ray detection elements, which detect the X-rays that have been generated from the X-ray generator and have passed through a subject, and from which detection signals are read out, are arranged in a grid shape in a channel direction perpendicular to a body axis of the subject and in a column direction along the body axis of the subject;
a data-acquisition module including a plurality of data-acquisition circuits configured to acquire the detection signals individually read out from the X-ray detection elements, to amplify the acquired detection signals individually, and to convert the detection signals to digital data, and a plurality of output modules configured to output the converted digital data individually; and
a reconstruction module configured to reconstruct a medical image, based on the output digital data,
wherein a plurality of systems of at least the data-acquisition circuits among the X-ray detection elements and the data-acquisition circuits are disposed in parallel per element of the X-ray detection elements in a center vicinity,
the X-ray detection elements are disposed at a higher density in the center vicinity in the channel direction than in parts different from the center vicinity, a pitch in the channel direction gradually decreases toward the center, and the pitch in the channel direction is substantially proportional to a square root of a distance from the center, and
each of the output modules, which are connected to the data-acquisition circuits disposed in parallel, is configured to output digital data obtained via the data-acquisition circuits.

2. The X-ray computed tomography apparatus of claim 1, wherein each of the output modules, which are connected to the data-acquisition circuits disposed in parallel, includes a plurality of input terminals electrically connected to output terminals of the data-acquisition circuits, and one output terminal electrically connected to the input terminals.

3. The X-ray computed tomography apparatus of claim 1, wherein each of the output modules, which are connected to the data-acquisition circuits disposed in parallel, is configured to average the digital data obtained via the data-acquisition circuits and to output the averaged digital data.

4. The X-ray computed tomography apparatus of claim 1, wherein, of the X-ray detection elements and the data-acquisition circuits, a plurality of systems of only the data-acquisition circuits are disposed in parallel per element of the X-ray detection elements in the center vicinity, and
the data-acquisition circuits disposed in parallel are disposed to be distributed to a plurality of chips.

5. The X-ray computed tomography apparatus of claim 1, wherein the data-acquisition circuits, which convert detection signals from the X-ray detection elements disposed at the higher density, are disposed to be distributed to plural chips.

6. An X-ray computed tomography apparatus comprising:
an X-ray generator configured to generate X-rays;
an X-ray detector configured such that a plurality of X-ray detection elements, which detect the X-rays that have been generated from the X-ray generator and have passed through a subject, and from which detection signals are read out, are arranged in a grid shape in a channel direction perpendicular to a body axis of the subject and in a column direction along the body axis of the subject;
a data-acquisition module including a plurality of data-acquisition circuits configured to acquire the detection signals individually read out from the X-ray detection elements, to amplify the acquired detection signals individually, and to convert the detection signals to digital data, and a plurality of output modules configured to output the converted digital data individually; and
a reconstruction module configured to reconstruct a medical image, based on the output digital data,
wherein a plurality of systems of at least the data-acquisition circuits among the X-ray detection elements and the data-acquisition circuits are disposed in parallel per element of the X-ray detection elements in a center vicinity,
the X-ray detection elements are disposed at a higher density in the center vicinity in the channel direction than in parts different from the center vicinity, a pitch in the channel direction gradually decreases toward the center, and the pitch in the channel direction is substantially proportional to a square root of a distance from the center, and
the reconstruction module is configured to reconstruct the medical image, based on digital data which are output via the output modules from the data-acquisition circuits disposed in parallel, and digital data which are output via the output modules from the data-acquisition circuits disposed in parts different from the center vicinity.

7. The X-ray computed tomography apparatus of claim 6, wherein the reconstruction module is configured to average digital data which are output via the output modules from the data-acquisition circuits disposed in parallel, and to reconstruct the medical image, based on digital data obtained by the averaging.

8. The X-ray computed tomography apparatus of claim 6, wherein, of the X-ray detection elements and the data-acquisition circuits, a plurality of systems of only the data-acquisition circuits are disposed in parallel per element of the X-ray detection elements in the center vicinity, and
the data-acquisition circuits disposed in parallel are disposed to be distributed to a plurality of chips.

9. An X-ray computed tomography apparatus comprising:
an X-ray generator configured to generate X-rays;
an X-ray detector configured such that a plurality of X-ray detection elements, which detect the X-rays that have been generated from the X-ray generator and have passed through a subject, and from which detection signals are read out, are arranged in a grid shape in a channel direction perpendicular to a body axis of the subject and in a column direction along the body axis of the subject;
a data-acquisition module including a plurality of data-acquisition circuits configured to acquire the detection signals individually read out from the X-ray detection elements, to amplify the acquired detection signals individually, and to convert the detection signals to digital data, and a plurality of output modules configured to output the converted digital data individually;
a preprocess module configured to preprocess the output digital data; and
a reconstruction module configured to reconstruct a medical image, based on the preprocessed digital data,
wherein a plurality of systems of at least the data-acquisition circuits among the X-ray detection elements and the data-acquisition circuits are disposed in parallel per element of the X-ray detection elements in a center vicinity,
the X-ray detection elements are disposed at a higher density in the center vicinity in the channel direction than in parts different from the center vicinity, a pitch in the channel direction gradually decreases toward the center, and the pitch in the channel direction is substantially proportional to a square root of a distance from the center, and
the preprocess module is configured to execute the preprocess, based on digital data which are output via the output modules from the data-acquisition circuits disposed in parallel, and digital data which are output via the output modules from the data-acquisition circuits disposed in parts different from the center vicinity.

10. The X-ray computed tomography apparatus of claim 9, wherein the preprocess module is configured to average digital data which are output via the output modules from the data-acquisition circuits disposed in parallel, and to execute the preprocess, based on digital data obtained by the averaging.

11. The X-ray computed tomography apparatus of claim 9, wherein, of the X-ray detection elements and the data-acquisition circuits, a plurality of systems of only the data-acquisition circuits are disposed in parallel per element of the X-ray detection elements in the center vicinity, and
the data-acquisition circuits disposed in parallel are disposed to be distributed to a plurality of chips.

12. The X-ray computed tomography apparatus of claim 9, wherein the data-acquisition circuits, which convert detection signals from the X-ray detection elements disposed at the higher density, are disposed to be distributed to plural chips.

13. An X-ray computed tomography apparatus comprising:
an X-ray generator configured to generate X-rays;
an X-ray detector configured such that a plurality of X-ray detection elements, which detect the X-rays that have been generated from the X-ray generator and have passed through a subject, and from which detection signals are read out, are arranged in a grid shape in a channel direction perpendicular to a body axis of the subject and in a column direction along the body axis of the subject;
a data-acquisition module including a plurality of data-acquisition circuits configured to acquire the detection signals individually read out from the X-ray detection elements, to amplify the acquired detection signals individually, and to convert the detection signals to digital data, and a plurality of output modules configured to output the converted digital data individually; and
a reconstruction module configured to reconstruct a medical image, based on the output digital data,
wherein a plurality of systems of at least the data-acquisition circuits among the X-ray detection elements and the data-acquisition circuits are disposed in parallel per element of the X-ray detection elements in a center vicinity, the data-acquisition circuits are disposed at a higher density in the center vicinity in the channel direction than in parts different from the center vicinity, a pitch in the channel direction gradually decreases toward the center, and the pitch in the channel direction is substantially proportional to a square root of a distance from the center, and each of the output modules, which are connected to the data-acquisition circuits disposed in parallel, is configured to output digital data obtained via the data-acquisition circuits.

14. An X-ray computed tomography apparatus comprising:

an X-ray generator configured to generate X-rays;

an X-ray detector configured such that a plurality of X-ray detection elements, which detect the X-rays that have been generated from the X-ray generator and have passed through a subject, and from which detection signals are read out, are arranged in a grid shape in a channel direction perpendicular to a body axis of the subject and in a column direction along the body axis of the subject;

a data-acquisition module including a plurality of data-acquisition circuits configured to acquire the detection signals individually read out from the X-ray detection elements, to amplify the acquired detection signals individually, and to convert the detection signals to digital data, and a plurality of output modules configured to output the converted digital data individually; and a reconstruction module configured to reconstruct a medical image, based on the output digital data, wherein a plurality of systems of at least the data-acquisition circuits among the X-ray detection elements and the data-acquisition circuits are disposed in parallel per element of the X-ray detection elements in a center vicinity, the data-acquisition circuits are disposed at a higher density in the center vicinity in the channel direction than in parts different from the center vicinity, a pitch in the channel direction gradually decreases toward the center, and the pitch in the channel direction is substantially proportional to a square root of a distance from the center, and the reconstruction module is configured to reconstruct the medical image, based on digital data which are output via the output modules from the data-acquisition circuits disposed in parallel, and digital data which are output via the output modules from the data-acquisition circuits disposed in parts different from the center vicinity.

15. An X-ray computed tomography apparatus comprising:

an X-ray generator configured to generate X-rays;

an X-ray detector configured such that a plurality of X-ray detection elements, which detect the X-rays that have been generated from the X-ray generator and have passed through a subject, and from which detection signals are read out, are arranged in a grid shape in a channel direction perpendicular to a body axis of the subject and in a column direction along the body axis of the subject;

a data-acquisition module including a plurality of data-acquisition circuits configured to acquire the detection signals individually read out from the X-ray detection elements, to amplify the acquired detection signals individually, and to convert the detection signals to digital data, and a plurality of output modules configured to output the converted digital data individually;

a preprocess module configured to preprocess the output digital data; and a reconstruction module configured to reconstruct a medical image, based on the preprocessed digital data, wherein a plurality of systems of at least the data-acquisition circuits among the X-ray detection elements and the data-acquisition circuits are disposed in parallel per element of the X-ray detection elements in a center vicinity, the data-acquisition circuits are disposed at a higher density in the center vicinity in the channel direction than in parts different from the center vicinity, a pitch in the channel direction gradually decreases toward the center, and the pitch in the channel direction is substantially proportional to a square root of a distance from the center, and the preprocess module is configured to execute the preprocess, based on digital data which are output via the output modules from the data-acquisition circuits disposed in parallel, and digital data which are output via the output modules from the data-acquisition circuits disposed in parts different from the center vicinity.

* * * * *